United States Patent
Reiley et al.

[11] Patent Number: 6,048,346
[45] Date of Patent: Apr. 11, 2000

[54] SYSTEMS AND METHODS FOR INJECTING FLOWABLE MATERIALS INTO BONES

[75] Inventors: Mark A Reiley, Piedmont; Arie Scholten, Fremont; Robert M Scribner, Los Altos; Michael L Reo, Redwood City, all of Calif.

[73] Assignee: Kyphon Inc., Menlo Park, Calif.

[21] Appl. No.: 08/910,809

[22] Filed: Aug. 13, 1997

[51] Int. Cl.[7] .................................................. A61B 17/58
[52] U.S. Cl. ................................. 606/92; 606/94; 606/83
[58] Field of Search .................................. 606/92, 94, 62, 606/67, 72, 83, 192; 623/19, 16, 22, 23; 604/56, 96; 222/391, 327

[56] References Cited

U.S. PATENT DOCUMENTS

| | | |
|---|---|---|
| 4,653,487 | 3/1987 | Maale . |
| 5,219,897 | 6/1993 | Murray ........................................ 606/94 |
| 5,468,245 | 11/1995 | Vargas, III ................................. 606/94 |

*Primary Examiner*—Michael Buiz
*Assistant Examiner*—Lien Ngo
*Attorney, Agent, or Firm*—Ryan Kromholz & Manion, S.C.

[57] ABSTRACT

A tube body includes an interior bore to carry a material flow into bone. The tube body includes a dispensing end having an opening communicating with the bore to dispense the material flow. One embodiment provides a cutting element, which extends in the opening to permit passage of the material flow and to sever the material flow in response to rotation of the tube body. Another embodiment deflects the dispensing end from the main axis of the tube body, to facilitate targeted introduction of flowable material, even when the access path does not align the tube body along the natural geometric axes of the treatment site. Another embodiment provides a connector having a rotating fitting, which releasably connects the tube body to a cement injecting tool. The rotating fitting allows the physician to rotate the injection nozzle assembly to control orientation and position in the treatment site, without rotating the associated injection tool itself.

28 Claims, 12 Drawing Sheets

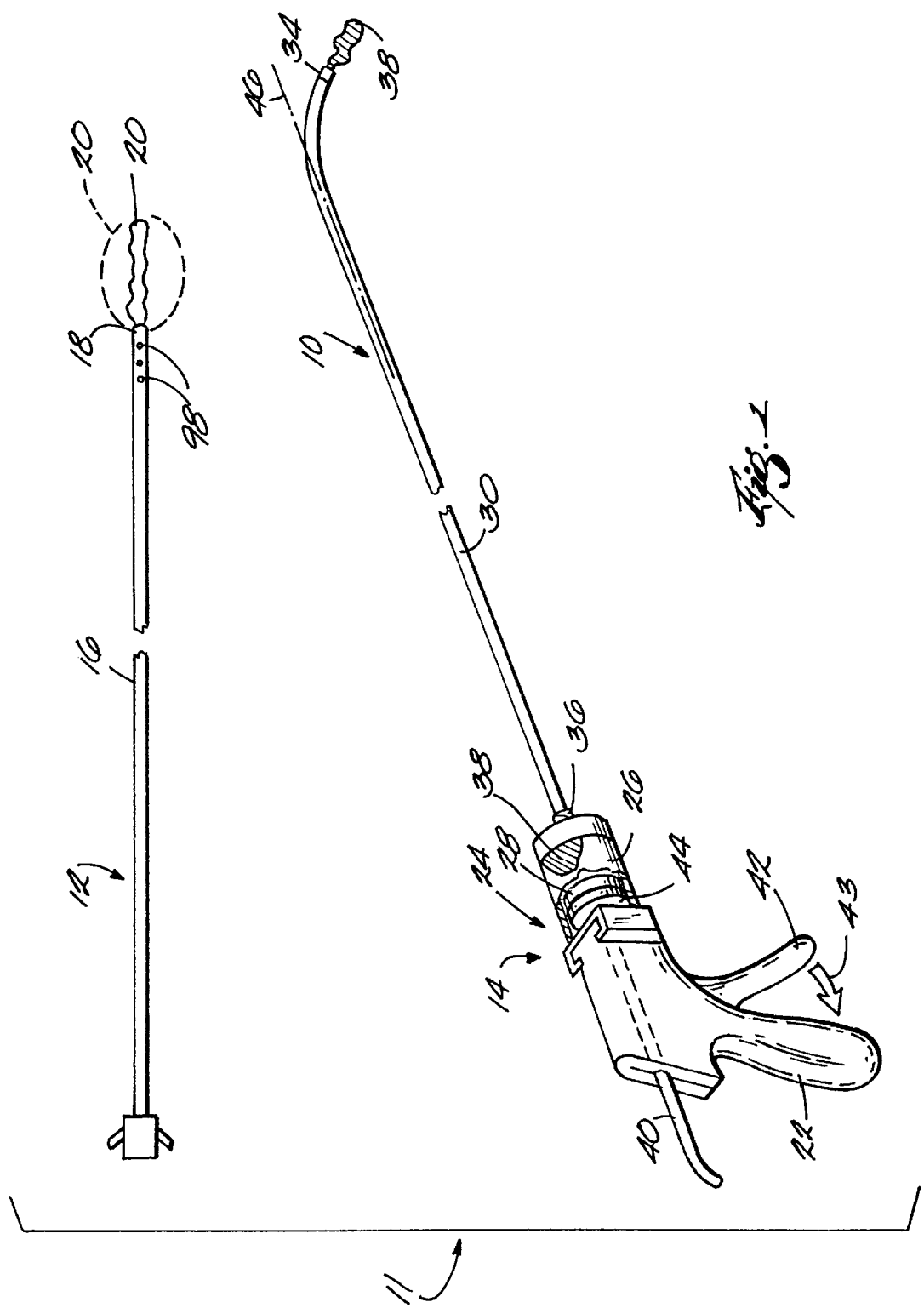

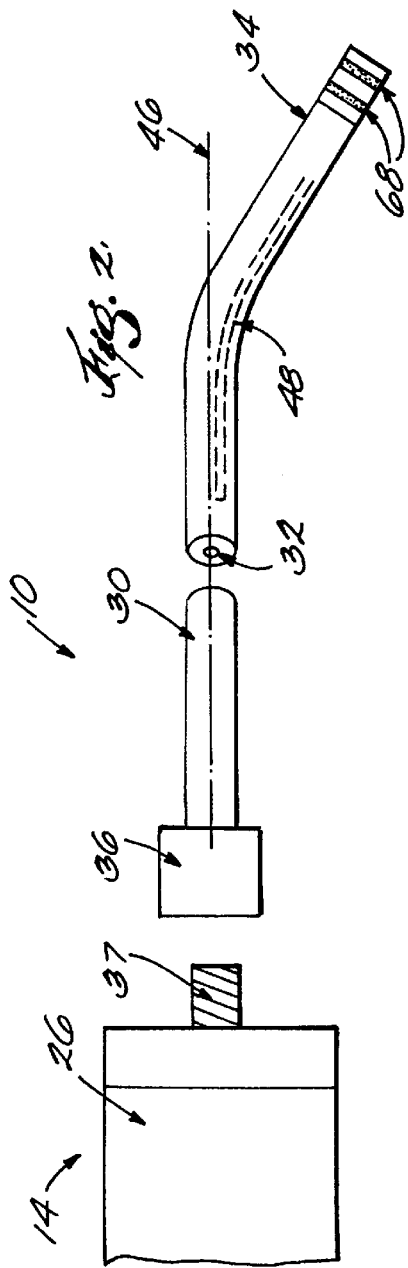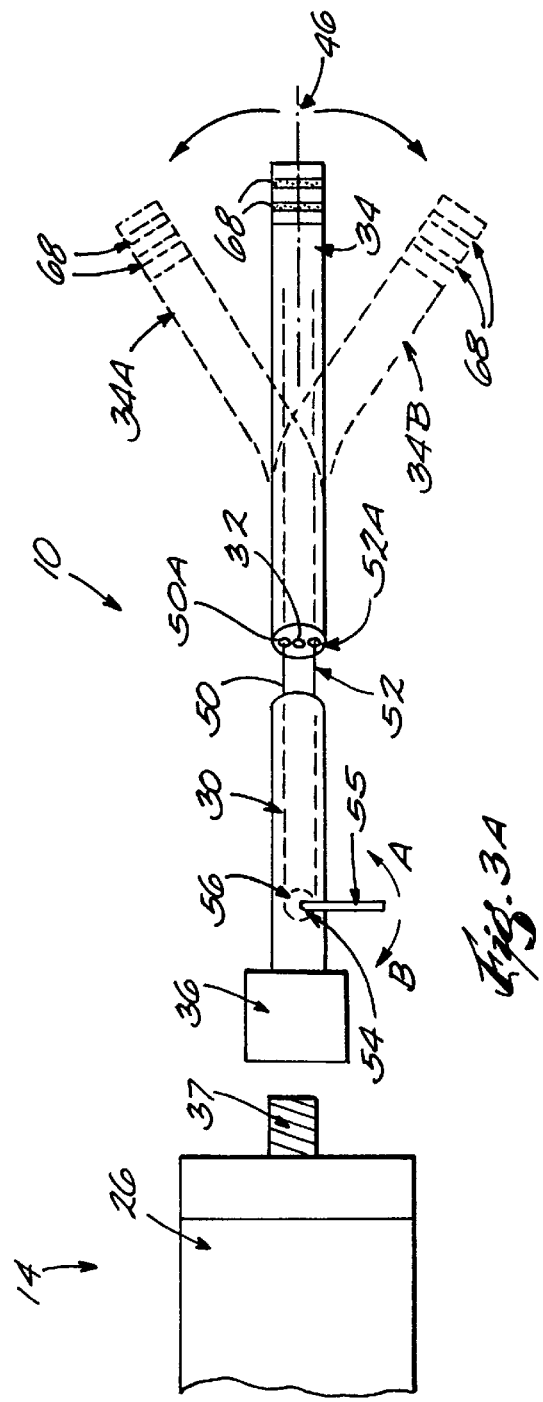

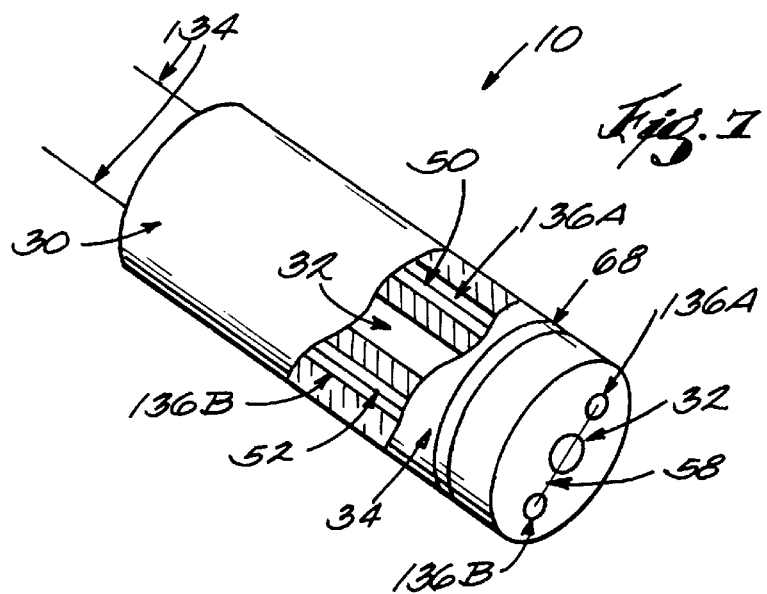
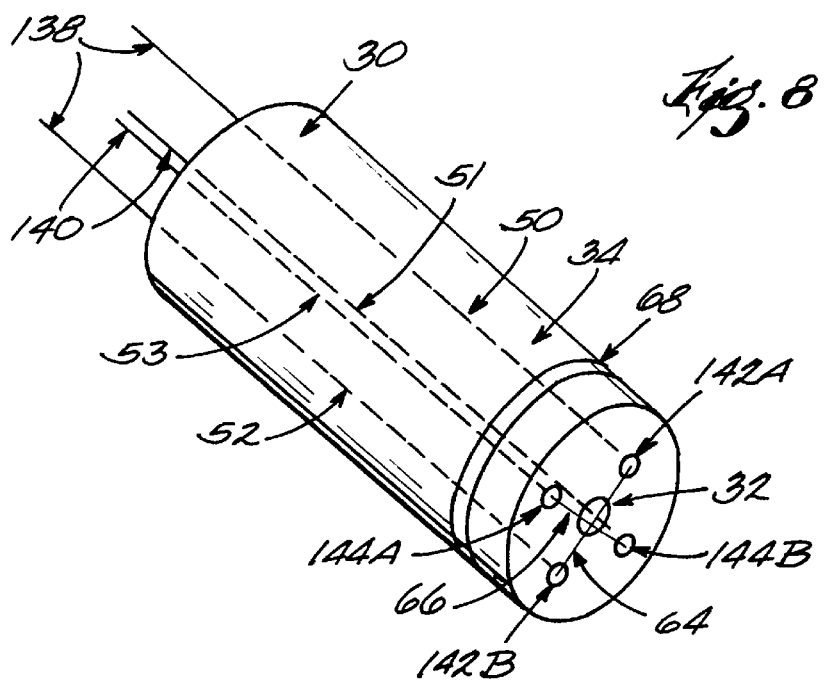

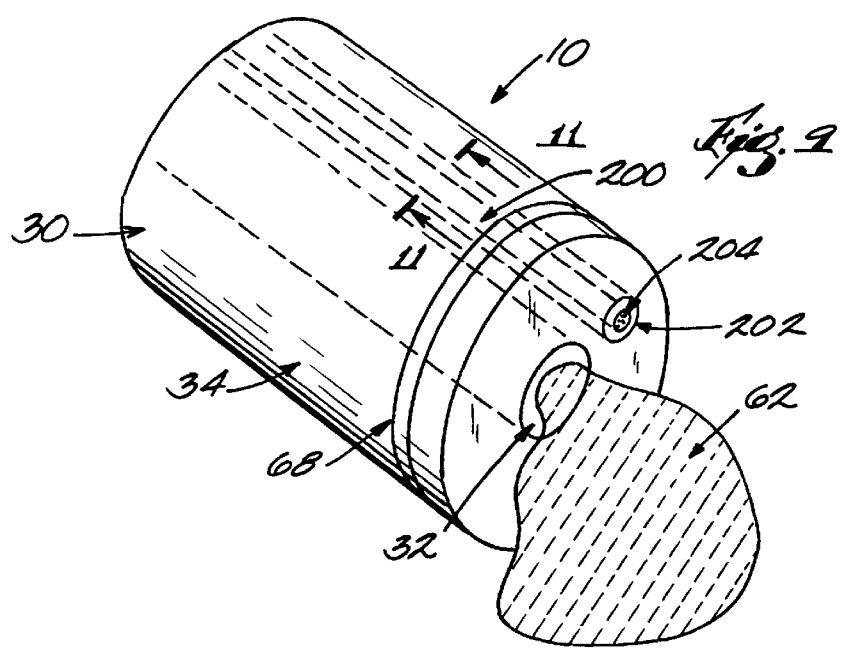
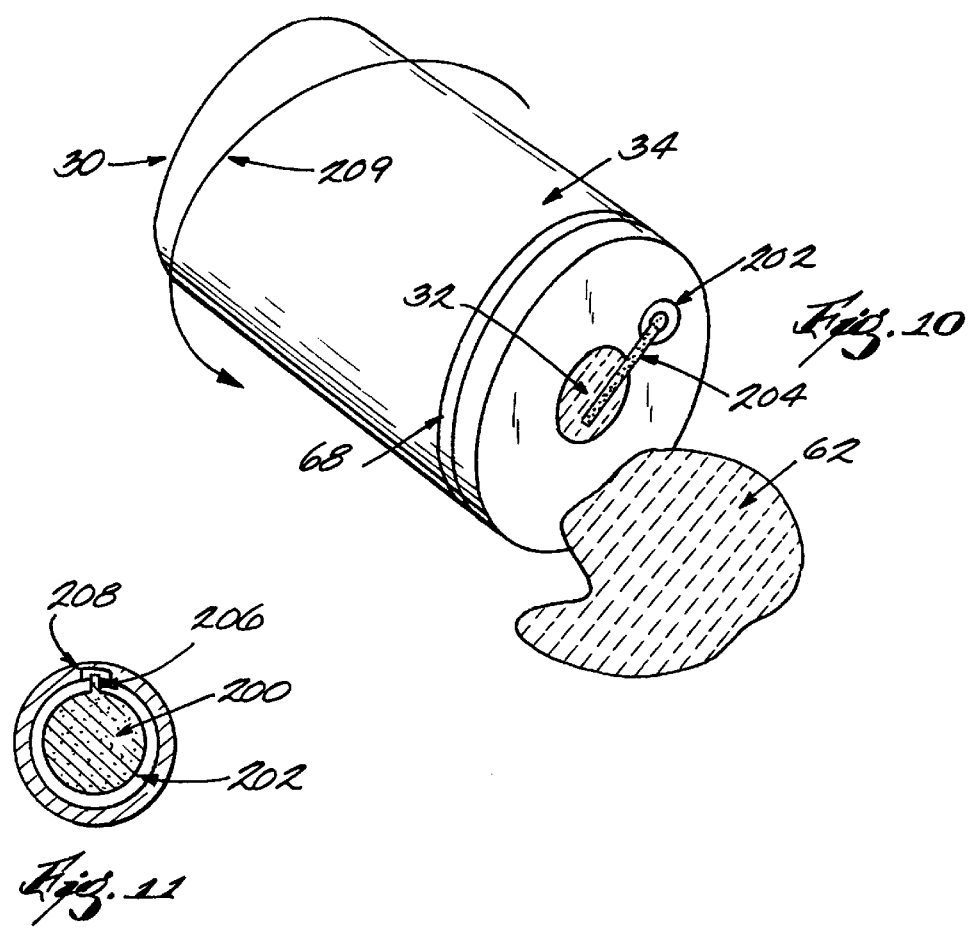

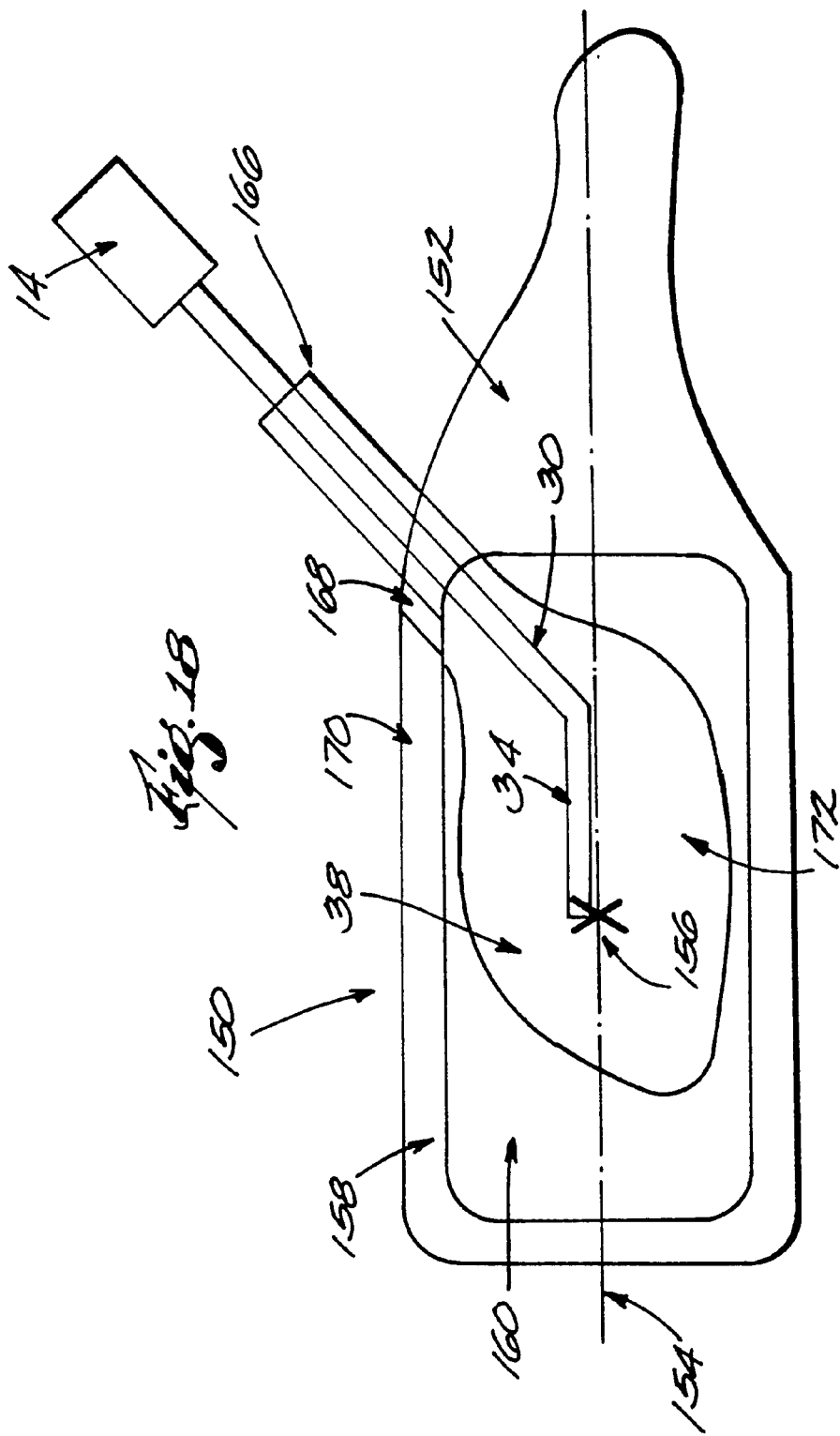

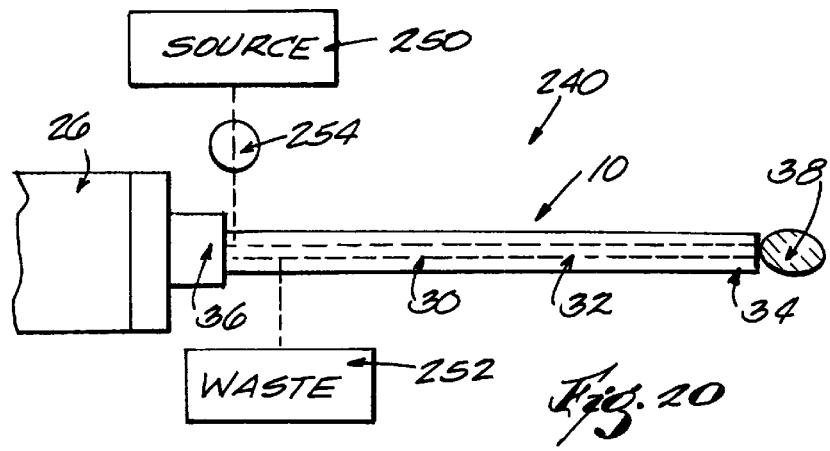
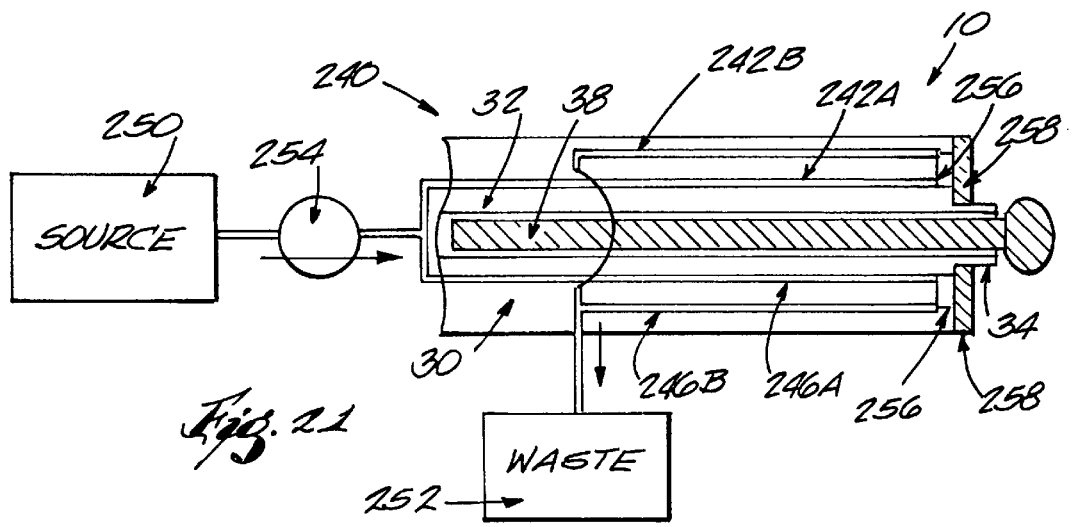
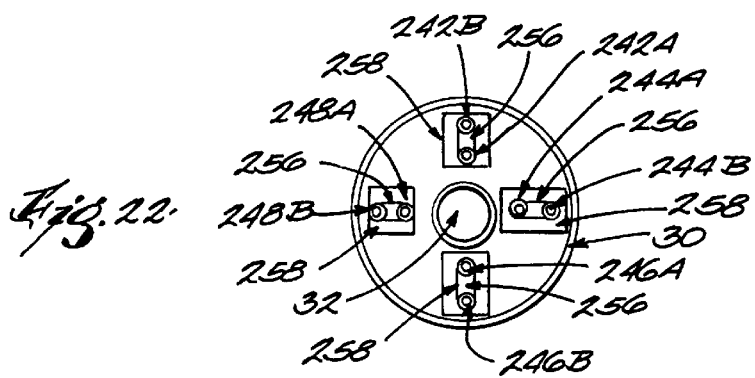

SYSTEMS AND METHODS FOR INJECTING FLOWABLE MATERIALS INTO BONES

FIELD OF THE INVENTION

The invention relates to the treatment of bone conditions in humans and other animals.

BACKGROUND OF THE INVENTION

Several companies offer mechanical bone cement injection devices. These devices are similar to a household caulking gun. Typically, the injection device has a pistol-shaped body, which supports a cartridge containing bone cement. The cement is typically in two-parts and must be mixed in a mixer and transferred into the cartridge for injection.

Just after mixing, and prior to curing, the cement is in a flowing, viscous liquid state, similar to a syrup or watery pancake batter in consistency. The injection device has a ram, which is actuated by a manually movable trigger or screwing mechanism for pushing the viscous bone cement out the front of the cartridge through a suitable nozzle and into the interior of a bone targeted for treatment.

Once injected into the targeted bone, the cement undergoes a curing cycle of perhaps 6 to 8 minutes. While curing, the cement passes from a viscous liquid to a putty-like consistency and finally to a hard rigid block.

SUMMARY OF THE INVENTION

The invention provides, in its various aspects, greater control over the placement of cement and other flowable liquids into bone.

One aspect of the invention provides an injector nozzle assembly for injecting flowable materials into bone. The assembly comprises a tube body including an interior bore to carry a material flow. The tube body includes a dispensing end having an opening communicating with the bore to dispense the material flow. According to this aspect of the invention, the assembly includes a cutting element, which extends in the opening to normally permit passage of the material flow, but which severs the material flow in response to rotation of the tube body. The cutting element provides the means, carried as an integral part of the nozzle assembly, to provide a consistently clean break between an expelled bolus of material and material residing in the tube body.

Another aspect of the invention provides an injector nozzle assembly in which the dispensing end of the tube body includes a side wall having an opening to dispense the material flow. According to this aspect of the invention, rotation of the tube body severs the material flow at the side opening.

Another aspect of the invention provides an injector nozzle assembly having a tube body and a dispensing end, which is deflected from the axis of the tube body. The deflection of the dispensing end permits targeted introduction of flowable material into the middle region of treatment site, even when the access path does not align the tube body itself along the natural geometric axes of the treatment site.

In one embodiment, material in the tube body is biased to deflect the dispensing end toward a normally deflected position. The material can comprise, e.g., memory wire carried in the tube body, or a thermally set condition.

In one embodiment, a guide sheath holds the tube body for sliding movement between first and second positions. In the first position, the dispensing end is confined within the guide sheath and moves within the guide sheath in a generally straightened orientation. In the second position, the dispensing end is moved outside the guide sheath and assumes the deflected position. The guide sheath permits deployment of the normally deflected dispensing end into bone by percutaneous access.

In another embodiment, the tube body carries at least one steering wire to deflect the dispensing end. In this embodiment, the assembly can include a mechanism on the tube body coupled to the steering wire to move the steering wire, and thereby selectively deflect the dispensing end.

According to another aspect of the invention, the injector nozzle assembly includes a connector to releasably connect the tube body to a cement injecting tool. In this aspect of the invention, the connector includes a rotating fitting to permit rotation of the tube body relative to the connector. Upon connection to an injection tool, such as a cement gun, the rotating fitting allows the physician to rotate the injection nozzle assembly to control orientation and position in the treatment site, without rotating the injection tool itself. Combined with a cutting element or a side dispensing opening, as described above, the physician can rotate the tube body to cut loose an expelled bolus of material, without rotating the injection tool.

In one embodiment, at least one of the rotating fitting and tube body includes indicia by which rotation or orientation of the dispensing end can be gauged, without need to visualize the dispensing end within the bone.

Another aspect of the invention provides an injector nozzle assembly which includes at least one interior lumen adapted to communicate with a source cooling fluid to circulate cooling fluid while the dispensing end dispenses a flowable material which generates heat.

Another aspect of the invention provides methods for injecting flowable materials into bone using a selected one of the injector nozzle assemblies previously described.

Features and advantages of the inventions are set forth in the following Description and Drawings, as well as in the appended Claims.

BRIEF DESCRIPTION OF THE DRAWINGS

FIG. 1 is a view of a system for treating bone, which includes a injector nozzle assembly embodying features of the invention;

FIG. 2 is an enlarged side view of the dispensing end of one embodiment of the injector nozzle assembly shown in FIG. 1, in which the dispensing end is prebent in a desired geometry to facilitate its deployment;

FIG. 3A is an enlarged side view of the dispensing end of another embodiment of the injector nozzle assembly shown in FIG. 1, in which the dispensing end is steerable to facilitate its deployment within bone;

FIG. 7 is an enlarged end view of the dispensing end of one embodiment of the injector nozzle assembly shown in FIG. 1, in which the dispensing end is steerable and also carries a loop formed for cutting cement free from the dispensing end;

FIG. 8 is an enlarged end view of the dispensing end of another embodiment of the injector nozzle assembly shown in FIG. 1, in which the dispensing end is steerable and also carries two loops formed for cutting cement free from the dispensing end;

FIG. 9 is an enlarged end view of the dispensing end of one embodiment of the injector nozzle assembly shown in FIG. 1, which carries a prebent stylet, which is shown in a retracted and straightened condition prior to use;

FIG. 10 is an enlarged end view of the dispensing end shown in FIG. 9, illustrating the rotation of the prebent stylet after advancement to cut free an ejected cement bolus;

FIG. 11 is a section view of the prebent stylet taken generally along line 11—11 in FIG. 9, showing a mating tab and keyway that prevents rotation of the stylet out of a desired orientation during use;

FIG. 18 is a lateral view of a vertebral body, partially cut away and in section, illustrating the deployment of the injector nozzle assembly shown in FIG. 1 by transpedicular access into a cavity previously formed by an expanded body;

FIG. 20 is a side view of a system which includes an injector nozzle assembly coupled to a source of cooling fluid to mediate the increase in temperature of curing cement dispensed by the assembly;

FIG. 21 is a somewhat diagrammatic side section view of the injector nozzle assembly shown in FIG. 20; and FIG. 22 is an end view of the injector nozzle assembly shown in FIG. 20.

Figure 3B:
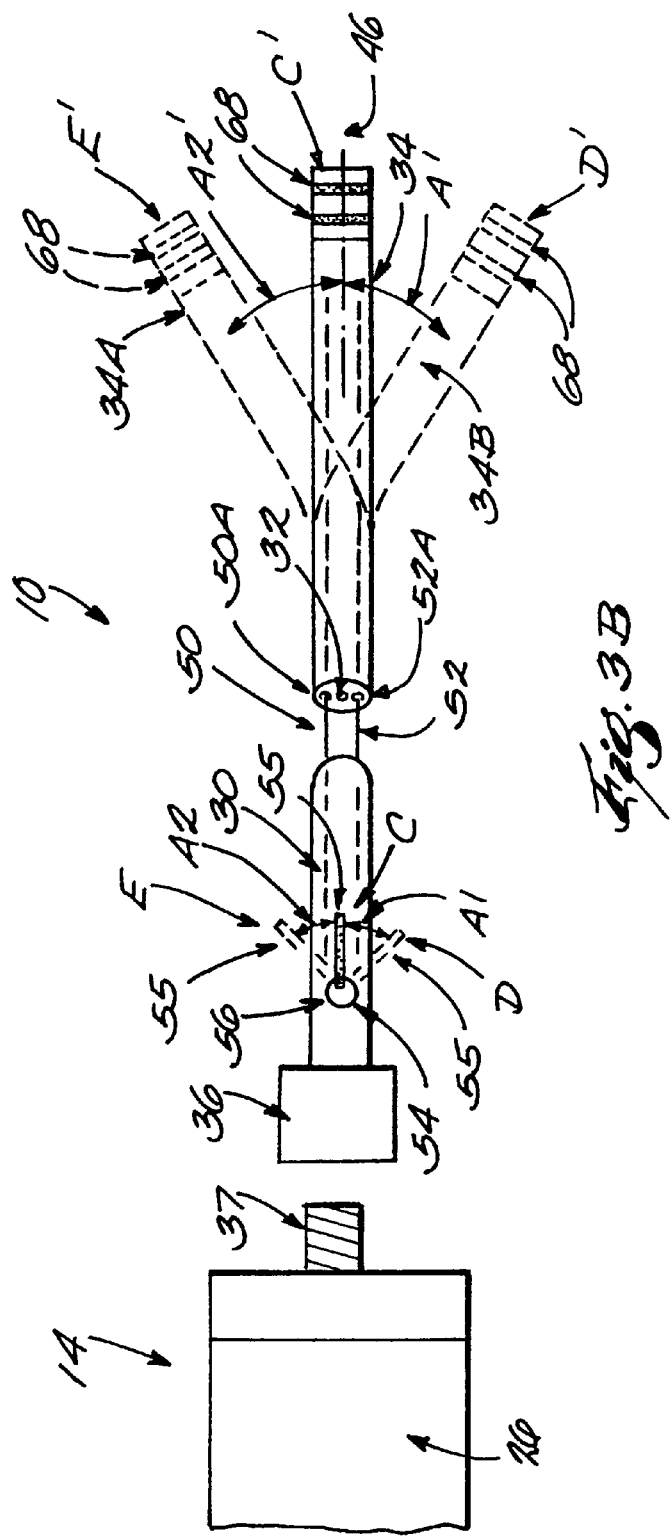
FIG. 3B is an enlarged side view of an alternative embodiment of a steerable dispensing end for the injector nozzle assembly shown in FIG. 1.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE PREFERRED EMBODIMENTS

FIG. 1 shows an injector nozzle assembly 10 for conveying a flowable material into bone. The assembly 10 is capable of carrying diverse types of flowable materials, e.g., bone cement or a suspension of one or more therapeutic substances, or both at the same time. The assembly 10 can likewise be used for diverse therapeutic purposes, as well, e.g., to treat a diseased bone, or to prevent or treat fracture or collapse of a bone, or both at the same time.

The illustrated embodiment shows the injector nozzle assembly 10 as part of a system 11, which injects cement for treating bone fracture or collapse, which is a purpose for which the assembly 10 is particularly well adapted. It should be appreciated, however, that the nozzle assembly 10 is not limited to use in the treatment of bone fractures or collapse.

FIG. 1 shows the system 11 to include a tool 12 that forms a cement-receiving cavity in cancellous bone and a tool 14, to which the assembly 10 is releasably attached to convey cement into the formed cancellous bone cavity.

In FIG. 1, the first tool 12 includes a catheter tube 16 having a distal end 18, which carries an expandable body 20. FIG. 1 shows the body 20 in a collapsed geometry, which permits the physician to insert the body 20 into the interior volume of a targeted bone. Once inserted into bone, the physician can convey fluid to expand the body 20, as shown in phantom lines in FIG. 1.

As will be described in greater detail later, expansion of the body 20 creates a cavity in cancellous bone. The use of expandable bodies to treat bones in this fashion is disclosed in U.S. Pat. Nos. 4,969,888 and 5,108,404, which are incorporated herein by reference.

The nozzle assembly 10 is deployed into the formed cavity to dispense bone cement, as will also be described in greater detail later. The cement cures and hardens to provide renewed interior structural support for cortical bone surrounding the cancellous bone.

Further details of the injection nozzle assembly 10 will now be described.

I. The Injection Nozzle Assembly

The injection nozzle assembly 10 is intended to be component that can be removably connected to a conventional injection tool 14, e.g., by a threaded connector 36 (see FIG. 2). As FIG. 1 shows, the tool 14 comprises a pistol-shaped grip, which will be referred to as a gun 22. The gun 22 includes an end fitment 24, to which a cartridge 26 is removably attached, for example, by threaded screw engagement (not shown). The cartridge 26 includes an interior, movable piston 28.

As FIG. 2 best shows, the nozzle assembly 10 comprises an injection tube 30. The injection tube is releasably coupled to the front end of the cartridge 26 by the threaded connector 36, which mates with a screw connector 37 on the cartridge.

The injection tube 30 includes a center lumen 32. The nozzle assembly 10 also includes a distal dispensing end 34, through which the center lumen 32 extends.

In use (see FIG. 1), the cartridge 26 contains bone cement 38. The cartridge 26 can be loaded with bone cement 38 in various way. For example, bone cement 38 is typically mixed in an external mixing device (not shown) from two components. Upon mixing, the two components begin to cure from a low viscosity, relatively free flowing liquid, like a thin pancake batter, to a substantially less flowable, putty like character. Eventually the cement 38 hardens to a rigid state within the targeted bone cavity formed by the expandable body 20.

Because of the increasing viscosity (lessening flow) of the bone cement 38, it should preferably be injected within a few minutes following mixing. For this purpose, a ran rod 40 extends within the gun 22. The rod 40 carries a ram disk 44. The rod 40 is coupled to a finger trigger 42.

When the physician pulls the trigger 42 rearward (as arrow 43 shows in FIG. 1), the rod 40 advances the ram disk 44 into contact with the cartridge piston 28. Advancement of the cartridge piston 28, in turn, pushes the bone cement 38 through the screw connector 37 into the lumen 32 of the injection tube 30 and out through the dispensing end 34, as FIG. 1 shows.

Details of the gun 22 can be conventional and are not essential to the invention. The gun 22 can comprise a cement gun made, for example, by Stryker Corporation (Kalamazoo, Mich.). This particular gun has a manually operated trigger with a mechanical advantage of about 9 to 1. Other injection guns may be used, having more or less mechanical advantage. Non-manually operated injection guns can also be used.

The nozzle assembly 10 can be constructed in various ways. For example, the injector tube 30, including its dispensing end 34, can be made of a plastic material, such as polyethylene or other suitable polymer. The diameter and length of the nozzle assembly 10 will vary according to the nature of the procedure. For example, for delivering cement in the hip region, the nozzle assembly 10 can be about 10 to 30 cm long with an outer diameter of about 4 to 12 mm. For delivering cement to a vertebral body, the nozzle assembly 10 can be about 18 to 30 cm long with an outer diameter of about 3 to 8 mm in diameter.

A. Deflecting the Dispensing End

As FIGS. 1 and 2 show, the dispensing end 34 of the nozzle assembly 10 is either deflected or is otherwise capable of being deflected outside the main axis 46 of the tube 30. The deflection defines a radius of curvature, which aids in the deployment of the dispensing end 34 within the targeted region. The advantages of the deflected dispensing end 34 will be discussed in greater detail later, as illustrated in the context of its deployment in a vertebral body.

The deflection of the distal tube end 36 can be accomplished in various ways, which the following description exemplifies.

(i) Fixed Deflection

In the embodiment shown in FIG. 2, the dispensing end 34 is normally biased into a prescribed deflected condition. The bias can be thermally set, using, for example, polyurethane or nylon material for the tube. Alternatively (as FIG. 2 shows), the dispensing end 34 can carry a length of prebent memory wire material 48, made from, e.g., a nickel-titanium alloy, which biases the dispensing end 34 toward the desired deflected geometry. The angle of the deflection can vary, according to the geometry at the intended treatment site.

As will be described in greater detail later, the bias is overcome by passage of the dispensing end 34 through a guide sheath, which temporarily straightens the dispensing end 34 during its deployment in the intended treatment site. When free of the confines of the guide sheath, the bias returns the dispensing end 34 to its preestablished deflected condition.

(ii) Adjustable Deflection

In an alternative embodiment, as FIG. 3A shows, the injection tube 30 carries steering wires 50 and 52. The steering wires 50 and 52 extend through side lumens, respectively 50A and 52A in the tube 30 and are coupled to the dispensing end 34.

In FIG. 3A, two steering wires 50 and 52 are shown for the purpose of illustration, but it should be realized that more or fewer steering wires may be used. The steering wires 50 and 52 are coupled to a steering mechanism 54 located on the proximal end of the tube 30 near the gun cartridge 26, for manipulation by the physician. In FIG. 3A, the steering mechanism 54 comprises a rotatable wheel 56 with a control lever 55, to which the steering wires 50 and 52 are coupled. Other types of steering mechanisms 54, such as pull tabs or linear actuators, can be used.

Counterclockwise rotation of the wheel 56 (arrow direction A) pulls on the first steering wire 50, deflecting the dispensing end 34 upward (phantom line position 34A in FIG. 3A). Clockwise rotation of the wheel 56 (arrow direction B) pulls on the second steering wire 52, deflecting the dispensing end 34 downward (phantom line position 34B in FIG. 3A). Multi-directional steering is thereby achieved.

In an alternative embodiment (see FIG. 3B), position of the control lever 55 corresponds with the angular orientation of the dispensing end 34. When the control lever 55 is located in the center position C, the dispensing end 34 is in a straightened condition C'. When the control lever 55 is moved down or clockwise (for example, to phantom line position D) the dispensing end 34 is likewise moved to phantom line position D', and the rotation angle A1 between position C and D generally corresponds with the deflection angle A1' between position C' and D'. Likewise, when the control lever 55 is moved up or counterclockwise (for example, to phantom line position E) the dispensing end 34 is likewise moved to phantom line position E', and the rotation angle A2 between position C and E generally corresponds with the deflection angle A2' between position C' and E'.

B. Cutting the Expelled Cement Bolus (i) Cutting Wires

Figure 4:
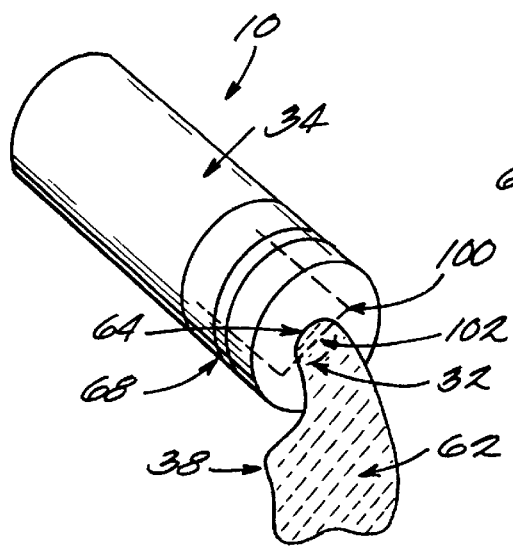
FIG. 4 is an enlarged end view of the dispensing end of one embodiment of the injector nozzle assembly shown in FIG. 1, which carries a loop formed for cutting cement free from the dispensing end.

As FIG. 4 shows, one embodiment of the nozzle assembly 10 includes a length of wire 100 carried by the dispensing end 34. The wire 100 extends across the central opening 32, forming a loop 102 for cutting loose the cement bolus 62 expelled through the lumen 32.

Figure 5:
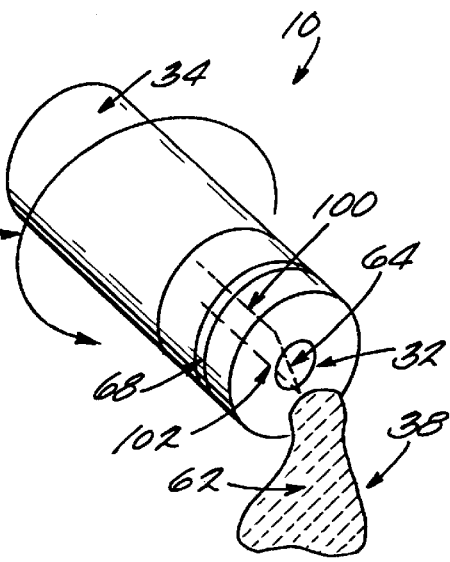
FIG. 5 is an enlarged end view of the dispensing end shown in FIG. 4, illustrating the rotation of the cement cutting loop to cut free an ejected cement bolus.

As FIGS. 4 and 5 show, rotation of the injection tube 30 (as arrow 60 in FIG. 5 shows) rotates the dispensing end 34 and, with it, the loop 102. The loop 102 rotates within the expelled bolus 62 of cement adjacent the terminal end of the lumen 32. Rotation of the loop 102 through 180° cuts loose the expelled cement bolus 62 from the unexpelled cement mass 64, which resides within the dispensing end 34. The loop 102, integrally carried by the dispensing end 34, creates a consistent and clean break between the expelled bolus 62 and the unexpelled mass 64.

Figure 6:
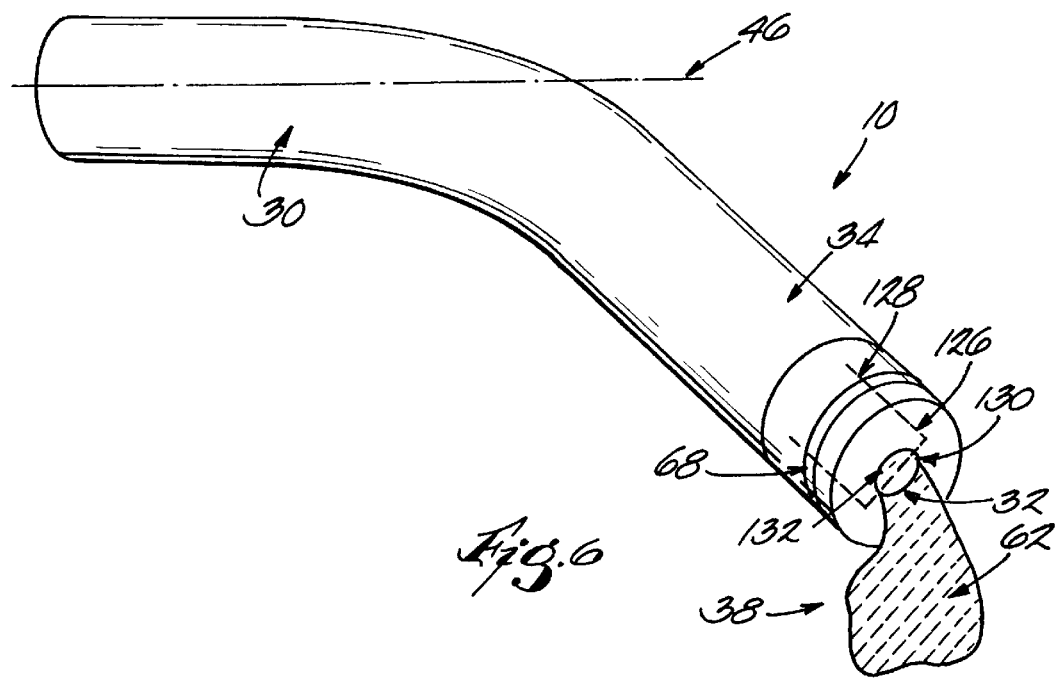
FIG. 6 is an enlarged end view of the dispensing end of one embodiment of the injector nozzle assembly shown in FIG. 1, which carries two crisscrossing loops formed for cutting cement free from the dispensing end.

In the embodiment shown in FIG. 6, the nozzle assembly 10 includes two lengths of wire 126 and 128 carried by the dispensing end 34. The wires 126 and 128 cross over the center lumen 32, forming two cement cutting loops 130 and 132 in the path of cement expelled by the lumen 32. Rotation of the dispensing end 34 through 90° passes the two loops 64 and 66 through the cement bolus 62, severing the cement bolus 62 from the cement mass residing in the dispensing end 34, in the manner shown in FIG. 5.

As FIG. 6 shows, the dispensing end 34 of the injection tube 30 shown in FIGS. 4 to 6 can, if desired, be preformed with a normal deflection, as previously described, to offset the dispensing end 34 with respect to the axis 46 of the injection tube 30. The tube 30 can also carry steering wires 50 and 52, as shown in FIG. 3, to steer the dispensing end 34.

Alternatively, the steering and cement cutting elements can be combined. For example, in the embodiment shown in FIG. 7, the nozzle assembly 10 includes a length of wire 134, which is threaded through side lumens 136A and 136B, which extend through the tube 30 (in the manner shown in FIG. 3). The wire 134 forms an exterior loop 58 at the tip of the dispensing end 34. In the illustrated and preferred embodiment, the side lumens 136A and 136B are generally diametrically spaced with respect to the center lumen 32, so that the exterior loop 58 extends across the center lumen 32, generally bisecting it. The exterior loop 58 serves as a cement cutting tool, as previously described.

In FIG. 7, the wire 134 is fixed to the tip of the dispensing end 34, so that pulling on either leg of the wire 134 will bend the dispensing end 134. The legs of the threaded wire 134 thereby serve as the first and second steering wires 50 and 52, which deflect the dispensing end 34 in the manner previously described and shown in FIG. 3.

FIG. 8 shows another alternative embodiment, in which two lengths of wires 138 and 140 are threaded through multiple pairs of side lumens 142A, 142B, 144A, and 144B, which extend through the tube 30. The wires 138 and 140 forming circumferentially spaced, multiple steering wires 50, 51, 52, and 53. The wires 138 and 140 also cross over the center lumen 32, forming two loops 64 and 66 across the dispensing end 34. The wires 138 and 140 are fixed by adhesive or other suitable manner to the tip of the dispensing end, forming multiple steering wire legs 50, 51, 52, 53. The fixed legs 50, 51, 52, and 53 provide multi-planar steering. The two loops 64 and 66 also serve as cement cutters.

FIGS. 9 to 11 show an alternative embodiment of a nozzle assembly 10, which includes a bent stylet 200 to cut loose an expelled cement bolus 62. The stylet 200 is slidably carried by an interior lumen 202 in the injection tube 30. As FIG. 11 best shows, a locating tab 206 on the stylet 200 mates with a groove or keyway 208 in the lumen 202, to prevent rotation of the stylet 200 in the lumen 202. A suitable push-pull mechanism (not shown) is accessible at the proximal end of the injection tube 30 to affect advancement and retraction of the stylet 200 in the lumen 202.

As FIG. 10 shows, the distal end 204 of the stylet 200 is preformed with an angle bend. When located in the lumen 202 (as FIG. 9 shows), the distal end 204 is retained in a straightened condition. When advanced free of the lumen 202, the distal end 204 assumes the preformed, bent configuration. The locating tab 206 and mating keyway 208 orient the stylet 200, so that, when moved free of the lumen 202, the distal end 204 bends toward and over the central opening 32 of the tube 32, as FIG. 10 shows. The distal end 204 preferably extends at least half way or more across the central opening 32 of the tube 30.

In use, while the distal stylet end 204 is withdrawn in the lumen 202, the cement bolus 62 is expressed from the central opening 32 of the dispensing end 34 (as FIG. 9 shows). When cement injection is completed, the physician slides the distal stylet end 204 forward from the lumen 202. The stylet end 204, freed from the lumen 202, bends over the central opening 32 into the cement bolus 62. Rotation of the dispensing end 34 through 360° (arrow 209 in FIG. 10) passes the distal stylet end 204 through the cement bolus 62, severing the bolus 62 from the cement mass in the dispensing end 34. The physician pulls on the stylet 200 to return the distal stylet end 204 to the lumen 202.

(ii) Side Injection Port

Figure 12:
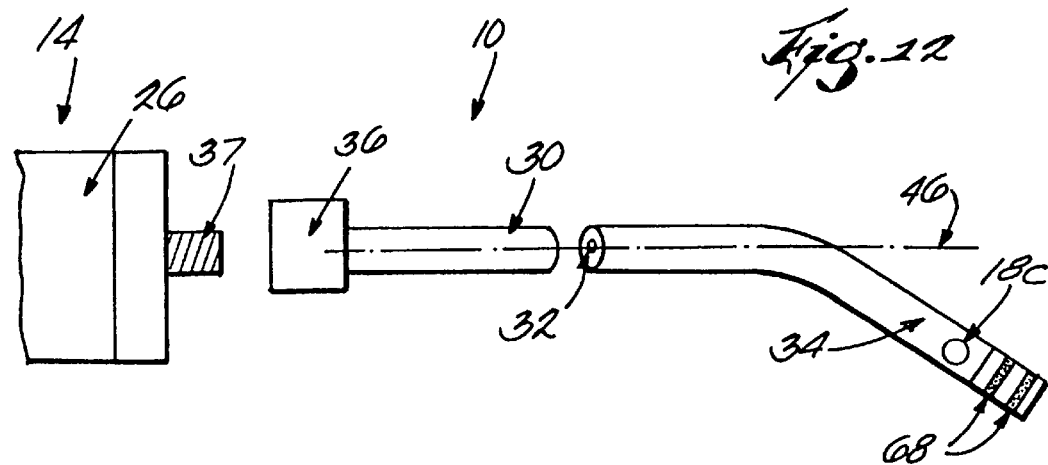
FIG. 12 is a side view of one embodiment of the injector nozzle assembly shown in FIG. 1, which includes a side port for dispensing cement.
Figure 13:
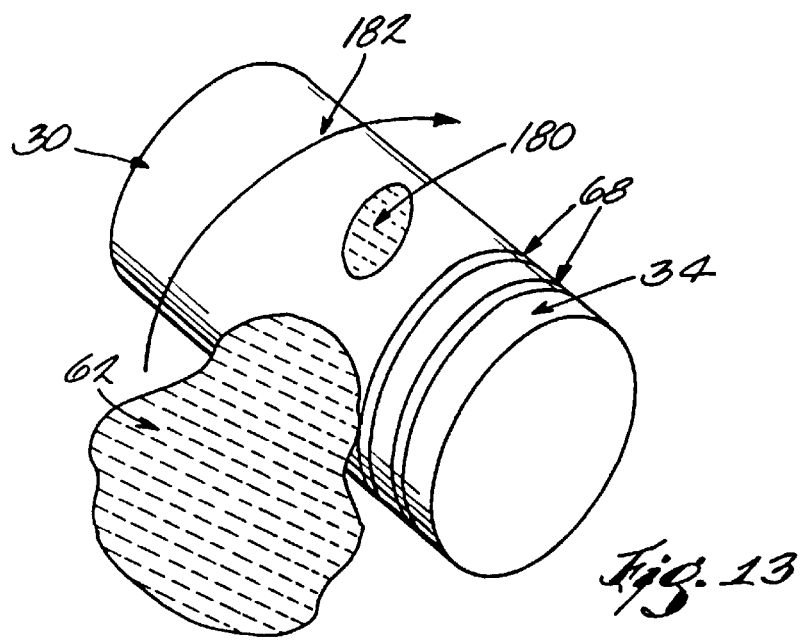
FIG. 13 is an enlarged end view of the injector nozzle assembly shown in FIG. 12, illustrating the rotation of the dispensing end to cut free an ejected cement bolus from the side dispensing port.

FIGS. 12 and 13 show another alternative embodiment of a nozzle assembly 10 which, upon rotation, cuts loose an expelled cement bolus 62.

In this embodiment, the nozzle assembly 10 includes an injection tube 30 like that shown in FIG. 2. The tube 30 includes a threaded connector 36, which screws onto the connector 37 of the cement gun cartridge 26. The tube 30 includes a center lumen 32 to transport cement from the cartridge 26 to a distal dispensing end 34.

Unlike the embodiment shown in FIG. 2, the center lumen 32 does not extend axially through the tip of the distal dispensing end 34. Instead, in FIGS. 12 and 13, the tip of the dispensing end 34 is closed and includes at least one dispensing port 180 extending at an angle from the central lumen 32. The port 180 opens on a side of the dispensing end 34.

As FIG. 13 shows, the cement bolus 62 is expressed through the side dispensing port 180, and not through the distal tip of the dispensing end 34. As FIG. 13 shows, rotation of the dispensing end 34 (indicated by arrow 182) moves the dispensing port 180 along an arc transversely of and away from the cement bolus 62. The transverse movement of the side dispensing port 180 away from the bolus 32 severs the bolus 32 from the cement mass residing in the center lumen 32.

As FIG. 12 shows, the dispensing end 34 of the injection tube 30 can, if desired, be preformed with a normal deflection, as previously described, to offset the dispensing end 34 with respect to the axis 46 of the injection tube 30. The tube 30 can also carry steering wires 50 and 52, as shown in FIG. 3, to steer the dispensing end 34.

(iii) Rotating Fitting

Figure 14:
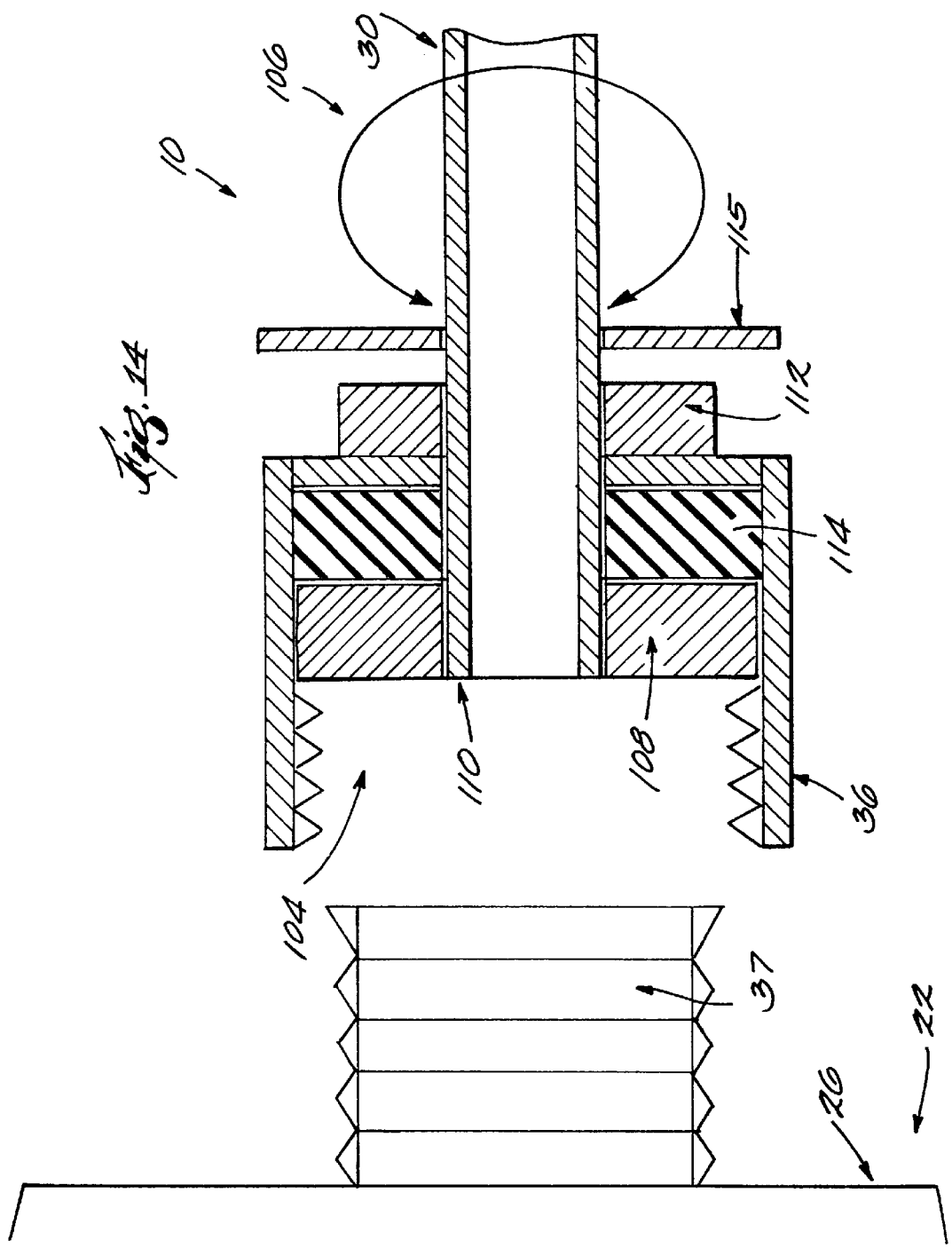
FIG. 14 is an enlarged side section view of an injector nozzle assembly which includes a rotating fitting that allows the injector tube to be rotated independent of the cement injecting tool.

As FIG. 14 shows, the threaded connector 36, which releasably couples the injection tube 30 to the screw connector 37 on the front end of the cartridge 26 of the cement gun 22, can include a fitting 104 that permits rotation of the injection tube 30 relative to the connector 36 and the gun 22.

Various constructions for the rotating fitting 104 are possible. In the illustrated embodiment, the rotating fitting 104 includes an adaptor 108 carried for rotation within the connector 36. The proximal end 110 of the injector tube 30 is secured to the adaptor 108 for common rotation. A retaining ring 112 outside the connector 36 surrounds tube 30, allowing its rotation but otherwise restraining rearward axial movement. An o-ring 114 is contained between the adaptor 108 and the end wall of the connector 36. The o-ring 114 restrains forward axial movement of the tube 30, while also preventing leakage of cement.

The rotating fitting 104 permits the physician to rotate the injection tube 30 with one hand, and thereby rotate the nozzle 34 (as arrows 106 show in FIG. 14), while holding the gun 22 stationary in another hand. As FIG. 14 shows, the injection tube 30 can carry a hub or grip 115 to facilitate rotation.

The rotating fitting 104 simplifies handling and manipulation of the cement injection tool 14 during rotation of the injection tube 30. The physician is able to rotate the injection tube 30, causing the one or more cement cutting loops carried by the rotating dispensing end 34 to cut loose an expelled cement bolus 62 (as shown in FIGS. 4 and 5, 9 and 10, and 12 and 13), without rotating the gun 22 itself. When combined with a deflected dispensing end 34, rotation of the tube 30 further helps locate the dispensing end 34 in the desired position, again without the need to rotate the gun 22.

Figure 15:
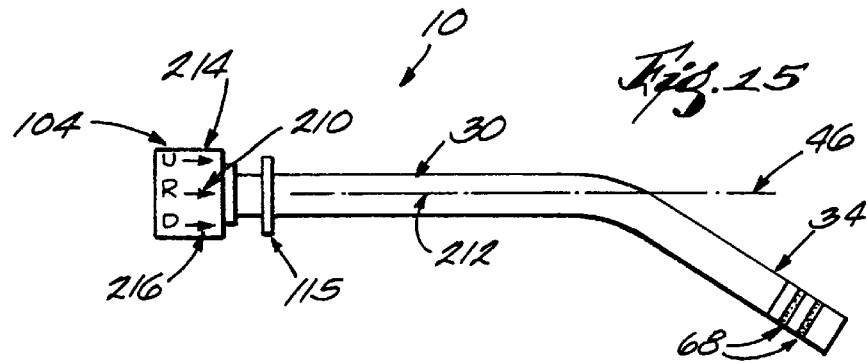
FIG. 15 is a side view of an injector nozzle assembly with a rotating fitting like that shown in FIG. 14, which includes index markers for ascertaining the orientation of the dispensing end and the extent to which the dispensing end is rotated, without need of direct visualization.

As FIG. 15 shows, the rotating fitting 104 can include indicia to gauge orientation or rotation of the injection tube 30. In the illustrated embodiment, the indicia includes an index mark 210 scribed on the connector 36, which aligns with an index mark 212 scribed on the proximal end of the injection tube 30. Alignment of the marks 210 and 212 places the dispensing end 34 in a particular, preestablished orientation.

For example, when the dispensing end 34 is normally biased in a deflected condition, as FIG. 15 shows, alignment of the marks 210 and 212 can designate that the deflection is to the right of the main axis 46. The index mark 210 can also include a visual or tactile identifier (for example, a raised letter "R" in FIG. 15) to further aid the physician in ascertaining the orientation.

The fitting 104 can also include additional auxiliary index marks (two of which 214 and 216 are shown in FIG. 15) and associated visual or tactile identifiers (respectively, "U" and "D"). Alignment of the mark 212 with auxiliary mark 214 indicates that the deflection orients the dispensing end 34 upward. Likewise, alignment of the mark 212 with auxiliary mark 216 indicates that the deflection orients the dispensing end 34 downward. Another auxiliary mark and associated identifier (not shown), located diametrically opposite to the mark 210, can also indicate a left orientation of the deflected dispensing end 34.

The alignment of the index mark 212 with the index marks 210, 214, and 216 allows the physician to remotely orient the deflected end 34 in a desired way, without reliance upon x-ray or other internal visualization technique. Tracking the rotation of the index mark 212 relative to one or more of the index marks 210, 214, or 216 also allows the physician to gauge the rotation of the injection tube 30, to achieve the degree of rotation necessary to cut the cement bolus 62 loose.

When the dispensing end 34 is steerable (as shown in FIG. 3), alignment of the marks 210 and 212 can designate that the steering wires 50 and 52 extend in a particular vertical or horizontal plane. With this orientation known, the physician can operate the steering mechanism 56 to achieve the desired bending action, without reliance upon x-ray or other form of internal visualization. Relative movement of the index marks also allows the physician to monitor the extent of rotation of the injection tube 30 when cutting the cement bolus 62 loose.

When the dispensing end 34 includes a side dispensing port 180 (as shown in FIGS. 12 and 13), alignment of the marks 210 and 212 can designate the orientation of the dispensing port 180, either left, right, up, or down. Relative movement of the index marks also allows the physician to monitor the extent of rotation of the injection tube 30 when cutting the cement bolus 62 loose.

C. Radiological Monitoring

In all the embodiments shown in FIGS. 2 to 15, the nozzle assembly 10 includes one or more radiological markers 68. The markers 68 are made from known radiopaque materials, like platinum, gold, calcium, tantalum, and other heavy metals. At least one marker 68 is placed at or near the dispensing end 34, to allow radiologic visualization of the dispensing end 34 within the targeted bone area.

Other forms of markers can be used to allow the physician to visualize the location of the dispensing end 34 within the targeted treatment area.

II. Deployment of Nozzle Assembly in a Vertebral Body

Figure 16:
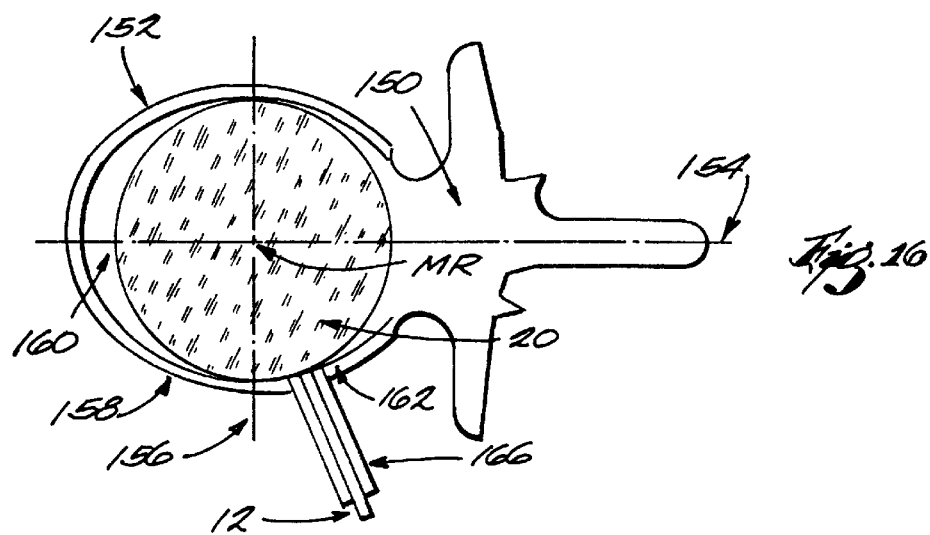
FIG. 16 is a coronal view of a vertebral body, partially cut away and in section, illustrating the deployment, by postero-lateral access, of an expandable body to compress cancellous bone and form an interior cavity.

Use of the nozzle assembly 10 will now be described when deployed in a human vertebra 150, which FIG. 16 shows in coronal (top) view. It should be appreciated, however, the nozzle assembly 10 is not limited in its application to vertebrae. The system 10 can be deployed equally as well in long bones and other bone types.

The vertebra 150 includes a vertebral body 152, which extends on the anterior (i.e., front or chest) side of the vertebra 150. The vertebral body 152 includes an exterior formed from compact cortical bone 158. The cortical bone 158 encloses an interior volume of reticulated cancellous, or spongy, bone 160 (also called medullary bone or trabecular bone).

The vertebral body 152 is in the shape of an oval disk, which is generally symmetric about an anterior-posterior axis 154 and a mid-lateral axis 156. The axes 154 and 156 intersect in the middle region or geometric center of the body 152, which is designated MR in the drawings.

As FIG. 16 shows, access to the interior volume of the vertebral body 152 can be achieved. e.g., by drilling an access portal 162 through a side of the vertebral body 152, which is called a postero-lateral approach. The portal 162 for the postero-lateral approach enters at a posterior side of the body 152 and extends at angle forwardly toward the anterior of the body 152. The portal 162 can be performed either with a closed, mininimally invasive procedure or with an open procedure.

As FIG. 16 shows, a guide sheath 166 is located in the access portal 162. Under radiologic, CT, or MRI monitoring, the tool 12 is introduced through the guide sheath 166, with the expandable body 20 collapsed. When deployed in the cancellous bone 160, the physician conveys a pressurized fluid into the body 20 to expand it. The fluid is preferably radio-opaque to facilitate visualization. For example, RenografinTM contract media can be used for this purpose.

Expansion of the body 20 within the interior volume compresses cancellous bone 160 to form a cavity 164. The compaction of cancellous bone also exerts interior force upon cortical bone 158, making it possible to elevate or push broken and compressed bone back to or near its original prefracture position.

The body 20 is preferably left inflated for an appropriate waiting period, for example, three to five minutes, to allow coagulation inside the vertebral body 152. After the appropriate waiting period, the physician collapses the body 20 and removes it. As FIG. 17 shows, the formed cavity 164 remains in the interior volume of the vertebral body 152.

Figure 17:
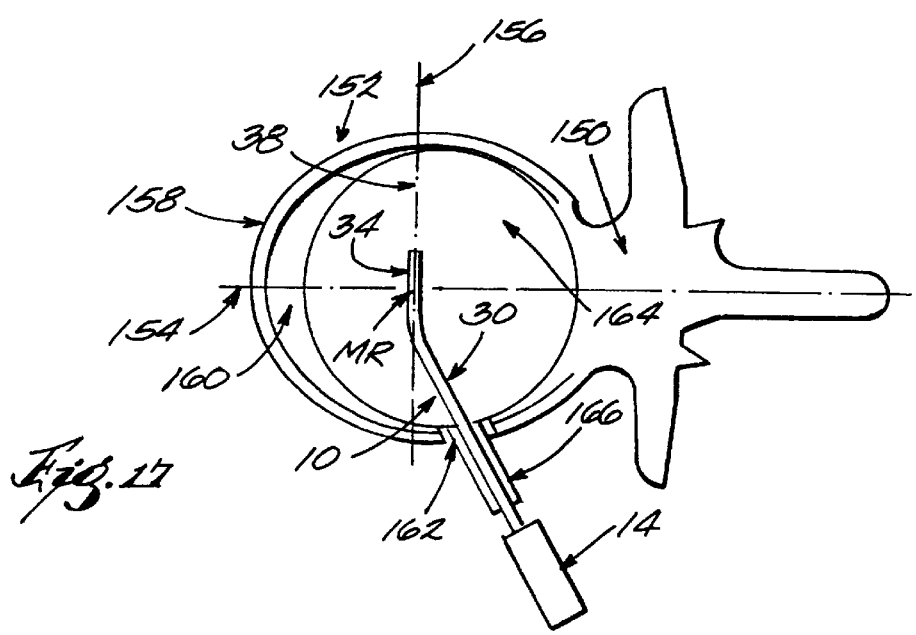
FIG. 17 is a coronal view of the vertebral body shown in FIG. 16, illustrating the deployment of the injector nozzle assembly shown in FIG. 1 by postero-lateral access.

As FIG. 17 shows, the second tool 14 is now readied for deployment. With the cartridge 26 filled with cement 38, the physician directs the injection tube 30 through the guide sheath 166 into the formed cavity 164.

If the dispensing end 34 is normally biased into a bent condition (as exemplified in FIG. 2), passage through the guide sheath 166 overcomes the bias and straightens out the dispensing end 34. Once free of the guide sheath 166, the dispensing end 34 returns to its normally biased condition.

Figure 19A:
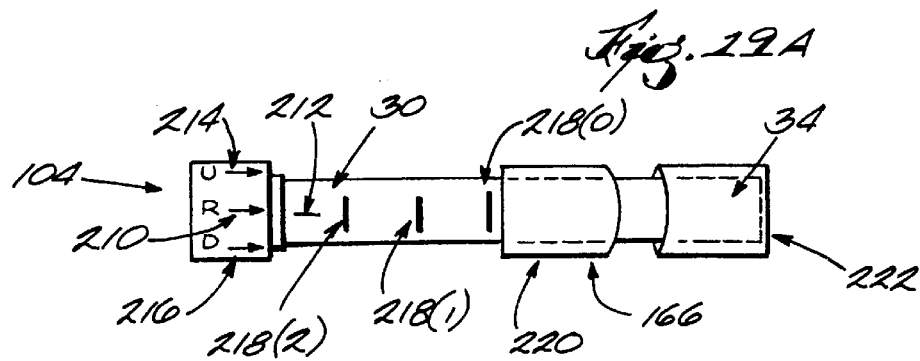
FIGS. 19A, 19B, and 19C are side views of an injector nozzle assembly, which also includes index markers for ascertaining the extent to which the dispensing end is extended into the targeted treatment site, without the need for direct visualization.
Figure 19B:
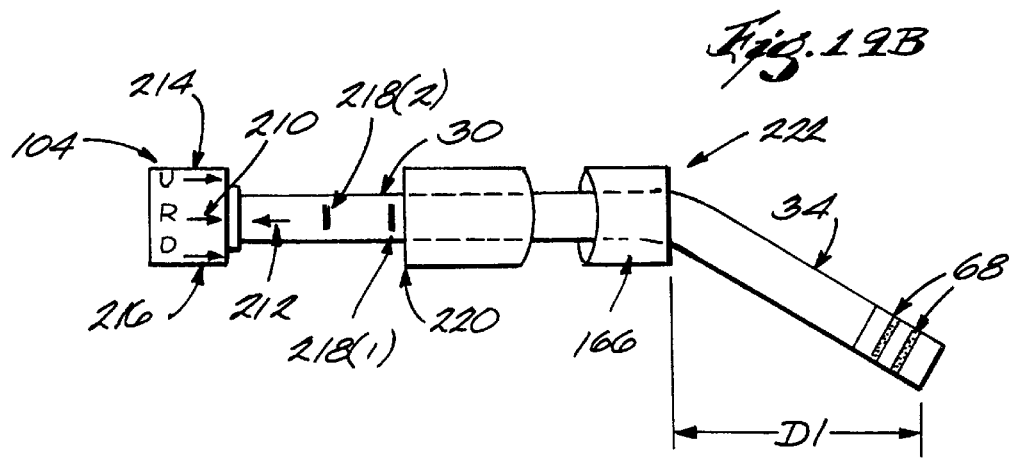
Figure 19C:
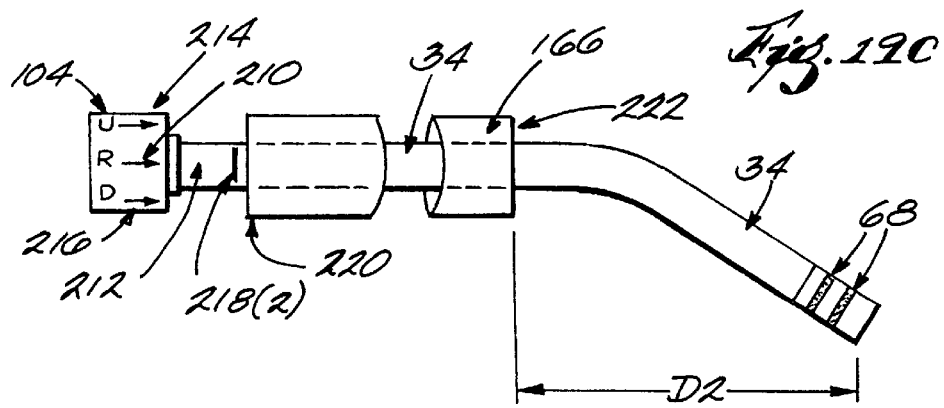

As shown in FIGS. 19A, 19B, and 19C, the tube 30 can include prepositioned markers 218(0) to 218 (2) along its length. The markers 218(0) to 218(2) are positioned to successively align with the proximal edge 220 of the guide sheath 166 at intervals that mark the extent to which the dispensing end 34 extends beyond the distal edge 222 of the guide sheath 166.

As FIG. 19A shows, when marker 218(0) and the proximal edge 220 align, the distal edge 222 of the guide sheath 166 and the dispensing end 34 are coincident (i.e., the tip of the dispensing end 34 coterminous with the distal edge 222 of the sheath 166).

As FIG. 19B shows, subsequent movement of the tube 30 in the sheath 166 brings the marker 218(1) into alignment with the proximal edge 220. This alignment indicates that the tip of the dispensing end 34 projects beyond the distal edge 222 by a first, predetermined distance D1.

As FIG. 19C shows, subsequent movement of the tube 30 to further advance the dispensing end 34 brings the marker 218(2) into alignment with the proximal edge 220. This alignment indicates that the dispensing end 34 projects beyond the distal edge 222 by a second, predetermined distance D2.

Of course, the number and spacing of the markers 218 can vary. The markers 218 allow the physician to gauge when and to what extent the dispensing end 34 projects into the targeted site, without need for direct visualization.

Under radiologic visualization provided by the markers 68, the physician may rotate the injection tube 30. Rotation of the injection tube 30 orients the dispensing end 34 within the cavity 164 before or during the injection of cement 38. In the embodiment shown in FIG. 14, the rotation may be accomplished without rotating the gun 22. In the embodiment shown in FIG. 15, the extent of rotation and the orientation of the dispensing end 34 can be observed using the markers 212/210, 214, and 216 on the fitting 104 (see FIG. 15), without active internal visualization.

Alternatively, if the tube 30 carries one or more steering wires 50 and 52 (as exemplified in FIG. 3), the physician may selectively bend the dispensing end 34 under radiological visualization provided by the markers 68. In this way, the physician can steer the dispensing end 34 into the desired position or positions within the cavity 164 before or during injection of cement 38. In the embodiment shown in FIG. 15, the markers 212/210, 214, and 216 on the fitting 104 aid the steering process (see FIG. 15), without active internal visualization.

As shown in FIG. 17, the postero-lateral access portal 162 does not align the injection tube 30 with the geometric axes 154 and 156 of the vertebral body 152. Nevertheless, deflection of the dispensing end 34 aligns the end 34 in the middle region MR of the body 152 along the mid-lateral axis 156.

As FIG. 17 shows, the gun 22 urges the cement 38, or other filling material, into the cavity 164. While injecting the material 38, the physician preferably begins with the dispensing end 34 positioned in the lateral region opposite to the access portal 162. As the material 38 flows into the cavity 164, the physician progressively moves the dispensing end 34 along the mid-lateral axis 156 through the middle region MR and toward the access portal 162. The deflection of the dispensing end 34 (by virtue of either the preformed bias or by active steering) allows the physician to maintain the desired alignment with the mid-lateral axis 156. The deflection of the dispensing end 34 (by virtue of either the preformed bias or by active steering) also allows the physician to keep the dispensing end 34 continuously submerged in the filling material 38, to thereby avoid the formation of air or fluid pockets.

The physician observes the progress of the injection radiologically using the markers 68, positioning the dispensing end 34 by rotation or steering, or both, as just described.

The physician flows material 38 into the cavity 164, until the material 38 reaches the interior end of the guide sheath 166. If the dispensing end 34 carries one or more exterior loops (as exemplified in FIGS. 4 to 10), or a side dispensing port 180 (as exemplified in FIGS. 12 and 13), rotation of the dispensing end 34 will cleanly sever the injected cement bolus residing in the cavity 164 from the unexpelled cement residing within the dispensing end 34 (as FIGS. 4 and 5 and FIGS. 12 and 13 show). In this way, cement residing in the cavity 164 will not be inadvertently drawn out of the cavity 164 upon withdrawal of the dispensing end 34. Rotation of the dispensing end 34 to sever the material bolus also avoids the formation of sharp pedicles in the material bolus, which could irritate surrounding tissue.

In the embodiment shown in FIG. 15, the markers 212/210, 214, and 216 on the fitting 104 aid in monitoring the extent of rotation, without active internal visualization.

As FIG. 18 shows in a lateral view, access into the interior volume of a vertebral body 152 can also be accomplished by drilling an access portal 168 through either pedicle 170. This is called a transpedicular approach. As FIG. 18 shows, the access portal 170 for a transpedicular approach enters at the top of the vertebral body 152, where the pedicle 170 is relatively thin, and extends at an angle downward toward the bottom of the vertebral body 152 to enter the interior volume.

The tool 12 is deployed through a guide sheath 166 in the portal 168 to form a cavity 172, in the same manner described above. The physician can manipulate the second tool 14 to steer the dispensing end 34 of the nozzle assembly 10 into the cavity 172. Although the transpedicular access portal aligns the tube 30 obliquely with respect to the axes 154 and 156, the deflected dispensing end 34 can be rotated into general alignment with either the anterior-posterior axis 154 or the mid-lateral axis 156 while injecting cement.

The deflected dispensing end 34 allows the introduction of cement 38 into the middle region MR of the vertebral body 152, using either postero-lateral access or a transpedicular access. The cement 28, when hardened, provides support uniformly across the middle region MR. The capability of the vertebral body 152 to withstand loads is thereby enhanced.

The above described procedure, carried out in a minimally invasive manner, can also be carried out using an open surgical procedure. Using open surgery, the physician can approach the bone to be treated as if the procedure is percutaneous, except that there is no skin and other tissues between the surgeon and the bone being treated. This keeps the cortical bone as intact as possible, and can provide more freedom in accessing the interior volume of the vertebral body 152.

III. Cooled Nozzle Assembly

After mixing and while curing, the cement 38 undergoes a chemical reaction that generates heat. When the cement temperature is below a given threshold value, the cement 38 maintains a flowing, viscous liquid state, which is suited for introduction through the nozzle assembly 10 into the targeted region. As the temperature increases beyond the threshold value, the cement 38 begins to harden, progressively losing its flow characteristic and becoming more resistant to passage through the nozzle assembly 10. It is desirable to expel the loose cement bolus 62 before the threshold temperature is reached.

FIG. 20 shows a system 240 for cooling the nozzle assembly 10 during passage of the cement 38 through the dispensing end 34. The system 240 includes the injection tube 30, which is releasably coupled to the front end of the cartridge 26 by the threaded connector 36, as previously described. The tube 30 includes the center lumen 30, through which cement 38 conveyed from the cartridge 26 passes.

The system 240 further includes at least one paired set of side lumens, which extend through the tube 30 axially beside the center lumen 30. In the illustrated embodiment (see FIG. 22), four paired lumen sets are shown, designated 242 A and B, 244 A and B, 246 A and B, and 248 A and B. As shown in FIGS. 21 and 22, each lumen set 242A/B; 244A/B; 246A/B; and 248A/B comprises a closed loop for carrying a cooling fluid from a source 250, through the tube 30, and to waste 252.

As best shown in FIG. 21, the lumen designated A in each set 242A/B; 244A/B; 246A/B; and 248A/B communicates at its proximal end with the cooling fluid source 250 via an in line pump 254. The lumen designated A in each set 242A/B; 244A/B; 246A/B; and 248A/B therefore comprises an inlet path for the cooling fluid.

As FIG. 21 also shows, the inlet lumen A of each set 242A/B; 244A/B; 246A/B; and 248A/B communicates at its distal end with the distal end of the lumen designated B in its respective set 242A/B; 244A/B; 246A/B; or 248A/B. As FIGS. 21 and 22 show, communication between the distal ends of the lumens A and B in each set 242A/B; 244A/B; 246A/B; and 248A/B is established by removing material between the lumens A and B to form a channel 256 between them, and laying a sealing material 258 over the channel 256. The proximal ends of the lumens B in each set 242A/B; 244A/B; 246A/B; and 248A/B communicate with waste 252. The lumen B of each set 242A/B; 244A/B; 246A/B; and 248A/B thereby comprises a return path for the cooling fluid.

At the source 250, the cooling fluid is at a desired temperature, which is cooler than the threshold temperature of the cement 38. For example, the source fluid can comprise tap water at a temperature of about 689° F. (20° C.). While cement 38 is conveyed by the center lumen 32 for discharge, the pump 254 conveys cooling fluid from the source 250 through the inlet paths 242A, 244A, 246B, and 248B. The return paths 242B, 244B, 246B, and 248B carry the cooling fluid to waste 252. The circulation of cooling fluid in the tube 30 along the center lumen 32 dissipates heat generated by the curing cement 38, to mediate the temperature increase in the curing cement 38. The circulation of cooling fluid thereby keeps the curing cement 38 in the center lumen 32 in a viscous flowing condition for a longer period of time.

In the illustrated embodiment (see FIGS. 20 and 21), the return paths 242B, 244B, 246B, and 248B convey cooling fluid to waste 252 downstream of proximal end of the center lumen 30. This quickens the discharge of heated return fluid from the tube 30 to thereby further minimize the temperature increase within the center lumen 32.

It should be appreciated that the system 250 can also include a cutting element to sever the cement flow in response to rotation of the tube 30, as well as means for deflecting the dispensing end 34, in any of the manners previously described.

The features of the invention are set forth in the following claims.

We claim:

1. An assembly for injecting flowable material into bone comprising
    a tube body including an interior bore to carry a material flow, the tube body including a dispensing end,
    an opening in the dispensing end communicating with the bore to dispense the material flow, and
    a cutting element extending in the opening adjacent the dispensing end to permit passage of the material flow and to sever the material flow adjacent the dispensing end in response to rotation of the tube body.

2. An assembly for injecting flowable material into bone comprising
    a tube body including an interior bore to carry a material flow, the tube body including a dispensing end,
    an opening in the dispensing end communicating with the bore to dispense the material flow, and
    a cutting element comprising a single wire filament extending in the opening to permit passage of the material flow and to sever the material flow in response to rotation of the tube body.

3. An assembly for injecting flowable material into bone comprising
    a tube body including an interior bore to carry a material flow, the tube body including a dispensing end,
    an opening in the dispensing end communicating with the bore to dispense the material flow, and
    a cutting element comprising more than one wire filament extending in the opening to permit passage of the material flow and to sever the material flow in response to rotation of the tube body.

4. An assembly according to claim 2 or 3 wherein the cutting element is secured to the dispensing end.

5. An assembly according to claim 2 or 3 and further including a connector to releasably connect the tube body to an injecting tool.

6. An assembly for injecting flowable material into bone comprising
    a tube body including an interior bore to carry a material flow, the tube body including a dispensing end,
    an opening in the dispensing end communicating with the bore to dispense the material flow, and
    a cutting element extending in the opening to permit passage of the material flow and to sever the material flow in response to rotation of the tube body, and
    a mechanism to deflect the dispensing end.

7. An assembly according to claim 6 wherein the mechanism comprises at least one steering wire in the tube body coupled to the dispensing end.

8. An assembly for injecting flowable material into bone comprising
    a tube body including an interior bore to carry a material flow, the tube body including a dispensing end,
    an opening in the dispensing end communicating with the bore to dispense the material flow, and
    a cutting element extending in the opening to permit passage of the material flow and to sever the material flow in response to rotation of the tube body, and
    a steering mechanism for deflecting the dispensing end through a range of deflected positions.

9. An assembly according to claim 8 wherein the steering mechanism includes an member movable through a range of positions each of which generally marks a position of the dispensing end within the range of deflected positions.

10. An assembly according to claim 2 or 3 or 9 or 8 wherein the tube body includes indicia to gauge extent of penetration of the dispensing end into bone.

11. A method for injecting flowable material into bone comprising the steps of
    deploying a tube body into bone, the tube body including a dispensing end having an opening to dispense a material flow and a cutting element extending in the opening adjacent the dispensing end,
    injecting a material flow into the bone through the opening, and rotating the dispensing end to move the cutting element through the material flow and thereby sever the material flow adjacent the dispensing end.

12. A method for injecting flowable material into bone comprising the steps of deploying a tube body into bone, the tube body including a dispensing end having an opening to dispense a material flow and a cutting element extending in the opening, injecting a material flow into the bone through the opening, rotating the dispensing end to move the cutting element through the material flow and thereby sever the material flow from the opening, and deflecting the dispensing end in the bone.

13. A method according to claim 12 and further including the step of gauging orientation of the dispensing end before, during, or after the deflecting step.

14. A method according to claim 13 wherein orientation of the dispensing end is gauged without visualizing the dispensing end in the bone.

15. A method according to claim 5 or 6 and further including the step of visualizing the dispensing end in the bone.

16. An assembly according to claim 1 wherein the cutting element comprises a single wire filament.

17. An assembly according to claim 1 wherein the cutting element comprises more than one wire filament.

18. An assembly according to claim 1 wherein the cutting element is secured to the dispensing end.

19. An assembly according to claim 1 and further including a connector to releasably connect the tube body to an injecting tool.

20. An assembly according to claim 1 and further including a mechanism for deflecting the dispensing end.

21. An assembly according to claim 20 wherein the mechanism comprises at least one steering wire in the tube body coupled to the dispensing end.

22. An assembly according to claim 1 and further including a steering mechanism for deflecting the dispensing end through a range of deflected positions.

23. An assembly according to claim 22 wherein the steering mechanism includes an member movable through a range of positions each of which generally marks a position of the dispensing end within the range of deflected positions.

24. An assembly according to claim 1 wherein the tube body includes indicia to gauge extent of penetration of the dispensing end into bone.

25. A method according to claim 11 and further including the step of deflecting the dispensing end in the bone.

26. A method according to claim 25 and further including the step of gauging orientation of the dispensing end before, during, or after the deflecting step.

27. A method according to claim 26 wherein orientation of the dispensing end is gauged without visualizing the dispensing end in the bone.

28. A method according to claim 11 and further including the step of visualizing the dispensing end in the bone.

* * * * *